(12) United States Patent
Bassin

(10) Patent No.: US 10,688,263 B2
(45) Date of Patent: Jun. 23, 2020

(54) ADJUSTMENT OF TARGET VENTILATION IN A SERVOVENTILATOR

(71) Applicant: ResMed Limited, Bella Vista (AU)

(72) Inventor: David John Bassin, Sydney (AU)

(73) Assignee: ResMed Pty Ltd (AU)

( * ) Notice: Subject to any disclaimer, the term of this patent is extended or adjusted under 35 U.S.C. 154(b) by 824 days.

(21) Appl. No.: 14/918,765

(22) Filed: Oct. 21, 2015

(65) Prior Publication Data

US 2016/0038698 A1 Feb. 11, 2016

Related U.S. Application Data

(63) Continuation of application No. 11/574,057, filed as application No. PCT/AU2005/001336 on Sep. 2, 2005, now Pat. No. 9,205,210.

(30) Foreign Application Priority Data

Sep. 3, 2004 (AU) ................................ 2004905022

(51) Int. Cl.
*A61M 16/00* (2006.01)

(52) U.S. Cl.
CPC .... *A61M 16/0069* (2014.02); *A61M 16/0003* (2014.02); *A61M 16/022* (2017.08); *A61M 16/0066* (2013.01); *A61M 2016/003* (2013.01); *A61M 2016/0021* (2013.01); *A61M 2016/0027* (2013.01); *A61M 2016/0039* (2013.01); *A61M 2205/3334* (2013.01); *A61M 2205/502* (2013.01)

(58) Field of Classification Search
CPC .............. A61M 16/00; A61M 16/0003; A61M 16/0051–0072; A61M 16/20–205; A61M 2016/0015–0033
See application file for complete search history.

(56) References Cited

U.S. PATENT DOCUMENTS

| 5,117,819 A | 6/1992 | Servidio et al. |
| 5,323,772 A | 6/1994 | Linden et al. |
| 5,494,028 A | 2/1996 | DeVries et al. |

(Continued)

FOREIGN PATENT DOCUMENTS

| CN | 1440302 A | 9/2003 |
| EP | 0520082 A1 | 12/1992 |

(Continued)

OTHER PUBLICATIONS

European Search Report dated Oct. 24, 2012.

(Continued)

*Primary Examiner* — Rachel T Sippel
(74) *Attorney, Agent, or Firm* — Botos Churchill IP Law LLP

(57) ABSTRACT

A servoventilator control slowly changes the target ventilation over a period of time, according to a preprogrammed schedule adapted to be set by the physician. Preferably, the target ventilation stays constant at an initial target ventilation for an initial hold time, and then increases at a constant rate until it reaches a final target ventilation, whereupon it stays constant thereafter. If the pressure support level is too high, possibly indicating glottic or upper airway closure, the rate of increase of target ventilation may be lowered or the final target ventilation not reached.

28 Claims, 2 Drawing Sheets

(56) References Cited

U.S. PATENT DOCUMENTS

| | | | |
|---|---|---|---|
| 5,682,878 | A | 11/1997 | Ogden |
| 6,401,713 | B1 | 6/2002 | Hill et al. |
| 6,467,477 | B1 | 10/2002 | Frank et al. |
| 6,532,956 | B2 | 3/2003 | Hill |
| 6,532,957 | B2 | 3/2003 | Berthon-Jones |
| 6,581,595 | B1 | 6/2003 | Murdock et al. |
| 6,644,312 | B2 | 11/2003 | Berthon-Jones et al. |
| 6,920,877 | B2 | 7/2005 | Remmers et al. |
| 7,013,892 | B2 | 3/2006 | Estes et al. |
| 2001/0027792 | A1 | 10/2001 | Berthon-Jones et al. |
| 2001/0035186 | A1 | 11/2001 | Hill |
| 2004/0016433 | A1* | 1/2004 | Estes .......... A61M 16/024 128/204.21 |
| 2004/0187870 | A1 | 9/2004 | Matthews et al. |

FOREIGN PATENT DOCUMENTS

| | | |
|---|---|---|
| JP | 2001-286564 A | 10/2001 |
| WO | 0202169 A1 | 1/2002 |
| WO | 03030804 A2 | 4/2003 |
| WO | 2003075991 A1 | 9/2003 |

OTHER PUBLICATIONS

International Search Report & Written Opinion for Application No. PCT/AU05/001336 dated Sep. 30, 2005.

Notice of Reasons for Rejection, Patent Application No. P2007-529304, Japanese Patent Office, dated Dec. 21, 2010.

\* cited by examiner

ADJUSTMENT OF TARGET VENTILATION IN A SERVOVENTILATOR

CROSS-REFERENCE TO RELATED APPLICATIONS

This application is a continuation of U.S. application Ser. No. 11/574,057, filed on Feb. 21, 2007, which is the national phase entry under 35 U.S.C. § 371 of International Application No. PCT/AU05/01336 filed Sep. 2, 2005, published in English, which claims priority from Australia Patent Application No. 2004905022 filed Sep. 3, 2004, all of which are incorporated herein by reference.

FIELD OF THE INVENTION

The present invention relates to the field of ventilatory assistance, and in particular, to methods and apparatus for determining suitable ventilator settings in patients with alveolar hypoventilation during sleep, and for delivery of those settings.

BACKGROUND OF THE INVENTION

In the field of noninvasive ventilation, for example as described in U.S. Pat. No. 6,532,957, a problem arises particularly in patients newly introduced to servoventilation. The patient's arterial CO2 partial pressure (PCO2) may be well above the value preferred by the clinician; for example, the PCO2 may be 60 mm Hg, and the clinician would prefer to stabilize it at 45 mm Hg. This would require the patient's alveolar ventilation to be increased by a factor of approximately 60/45=4/3. Yet if the clinician sets the target ventilation of the servoventilator to 4/3 of the patient's current ventilation, such a large increase in ventilation, if it occurs immediately, is likely to abolish all respiratory drive and much of the upper airway drive (leading to problems with upper airway obstruction). It may cause glottic closure, preventing the ventilation from increasing to the target level, despite the ventilator delivering the maximum level of pressure support for which it is programmed, which may lead to arousal from sleep. If the arterial pH is relatively normal at the beginning of therapy, indicating a metabolic compensation for a relatively chronic respiratory acidosis, a sudden large increase in ventilation would result in a marked alkalosis, with undesirable electrolyte shifts, including hypokalaemia, with the potential for inducing cardiac arrhythmias.

For these reasons a progressive increase of target ventilation over a period of time, typically several days or weeks, is desirable. This might be achieved by frequent manual changes of the target ventilation, but this would be inconvenient, since the patient is likely to be at home at this stage.

BRIEF SUMMARY OF THE INVENTION

In accordance with my invention, a servoventilator incorporates a mechanism for slowly changing the target ventilation over a period of time, according to a preprogrammed schedule set by the physician. In most cases the intention will be that the target ventilation increases over a period of time, from a first level to a second level, then stay at the second level thereafter. This increase could occur according to any arbitrary increasing function of time.

In one form of my invention, the target ventilation stays constant at a first level, $V_1$ (the initial target ventilation) for a fixed period of time (the initial hold time) until time $t=t_1$, which might be zero, then increases at a constant rate until it reaches a second level, $V_2$ (the final target ventilation), whereupon it stays constant thereafter.

The rate of increase, R may be calculated from the initial target ventilation $V_1$, the final target ventilation $V_2$, and a target ventilation ramp time $t_r$, all these settings being entered by the clinician using the following equations:

$$t_r = t_2 - t_1$$

$$R = \frac{V_2 - V_1}{t_r}$$

Various constraints may be added to modify the rate of increase of target ventilation. For example, if the pressure support level is too high, possibly indicating glottic or upper airway closure, the rate of increase of target ventilation may be lowered or even set to zero temporarily, so it takes longer to reach the final target ventilation, or in some cases the final target ventilation may never be achieved.

Figure 1:
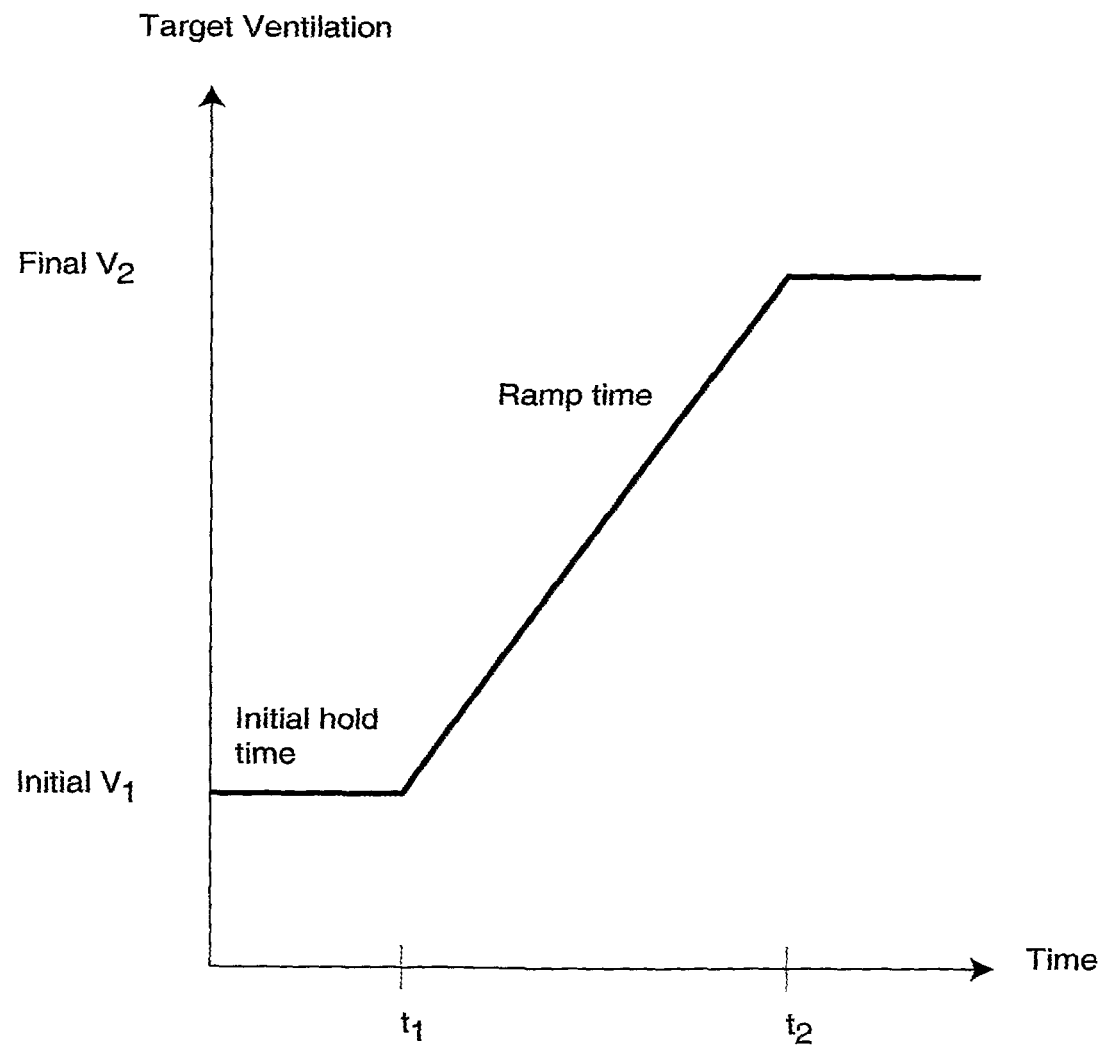
FIG. 1 illustrates an embodiment of my invention. The x-axis shows time, the y-axis shows ventilator target ventilation.
Figure 2:
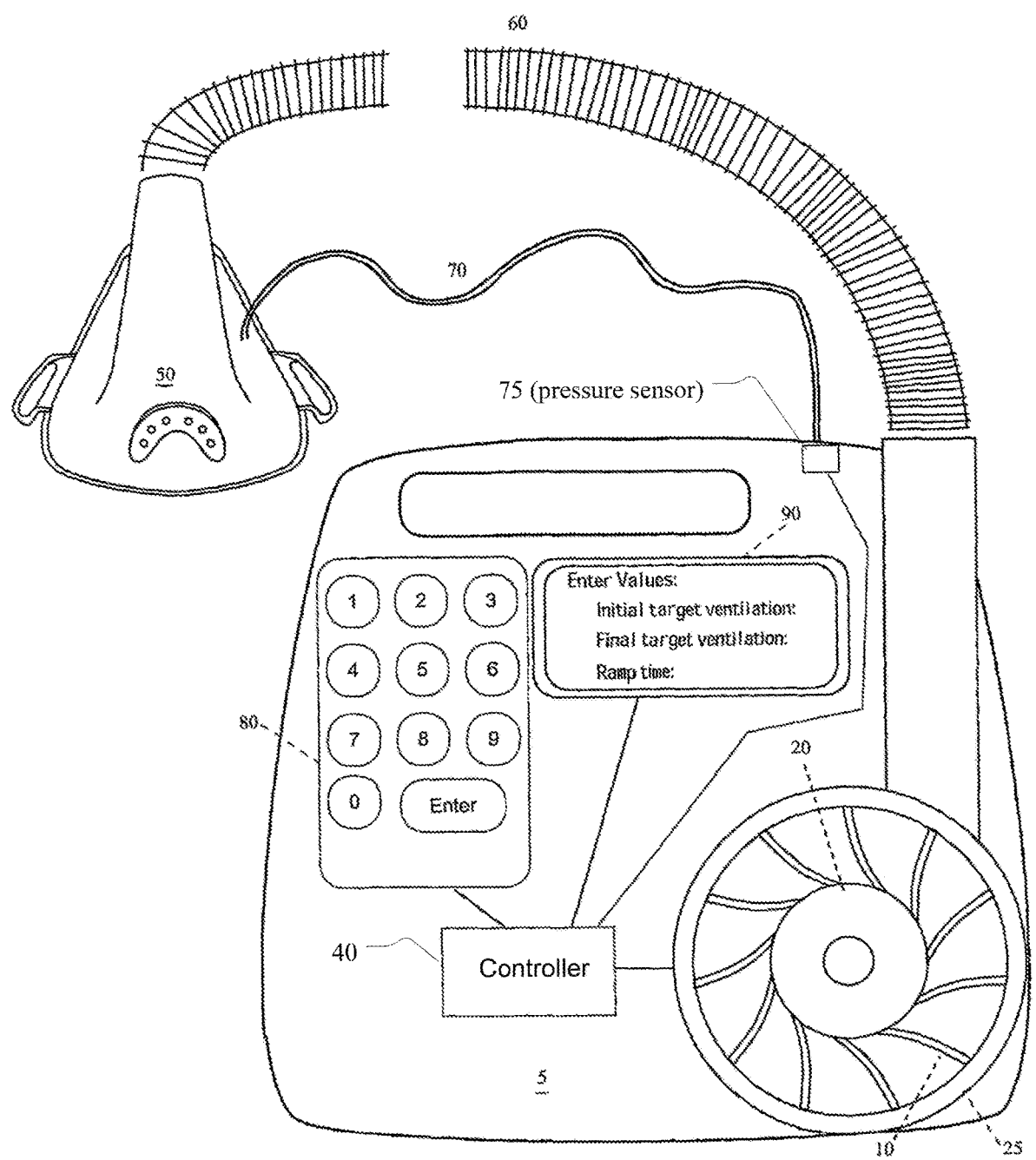
FIG. 2 illustrates servo-ventilator apparatus 5 suitable to perform the invention. An electric motor 20 has an impeller 10 and is under the control of a controller circuit 40. In use the motor and impeller is housed in a volute 25, which in use allows a flow of pressurized air to pass along the air delivery conduit 60 to a suitable patient interface 50. The patient interface 50 may be a nasal mask, or nose and mouth mask, a full-face mask or some other suitable device. A pressure sense tube 70 between the patient interface 50 and a pressure sensor 75 allows the controller 40 to sense pressure in the patient interface 50. The controller 40 can also determine the flow rate and of air along the air delivery conduit 60 via a flow sensor (not shown). The apparatus includes a display 90 and keyboard 80 which allow someone, for example a clinician, to set appropriate target ventilators and ramp times in accordance with an embodiment of the invention.

The determination of target ventilation settings may be accomplished as described in U.S. Pat. No. 6,644,312, the disclosure of which is incorporated by reference. In particular, suitable initial target ventilator settings for use with a servoventilator may be determined by measurements and observations made on the subject patient while awake during a learning period. Or, the target ventilation may be a fixed percentage of an average ventilation taken over a portion of the learning period. During the learning period the servo-control of ventilation is disabled, and the device is set to deliver a fixed minimum degree of support, typically 6 cmH2O chosen to make the patient feel comfortable. During this learning period, ventilation is measured and oxygen saturation levels may be measured by an oximeter. A target ventilation for use during sleep is selected or determined based on the ventilation measurements and optionally oxygen saturation measurements. Where the PCO2 of the subject patient would be higher than desired by the clinician, a final target ventilation can be determined by multiplying an initial target ventilation by the ratio of the PCO2 value to a desired PCO2 value.

A clinical algorithm embodying the invention is:
(i) use a suitable ventilator to learn the patient's awake ventilation (for example according to U.S. Pat. No. 6,644,312;
(ii) set the initial target ventilation to a proportion of this ventilation;
(iii) set the final target ventilation to the initial target ventilation multiplied by the ratio of the desired PCO2 to the current PCO2;
(iv) set the target ventilation ramp time to some suitable value, depending on the clinical urgency of lowering the PCO2 and the amount by which it is desired to lower the PCO2 (all else being equal, larger falls might be expected to take longer).

A similar principle can be applied to conventional bilevel ventilation. The pressure support level can be programmed, after an initial hold time, to increase at a certain rate until it reaches a final pressure support level.

Thus in accordance with my invention there is provided a method of non-invasive ventilation of a patient comprising the steps of:
(i) ventilating a patient at a first level of ventilation for a first duration; and
(ii) At the expiration of the first duration, changing the level of ventilation from the first level to a second level over a second duration.

In one form of the invention, the second duration may be several weeks. In a preferred form, the change in level of ventilation is an increase. In one preferred form of the invention, the change in level of ventilation is automatically controlled.

Although my invention has been described with reference to particular embodiments, it is to be understood that these embodiments are merely illustrative of the application of the principles of the invention. Numerous modifications may be made therein and other arrangements may be devised without departing from the spirit and scope of the invention.

The invention claimed is:

1. A servo-ventilator apparatus for controlling pressure support ventilation provided, via a patient interface, to a patient with alveolar hypoventilation during sleep, the servo-ventilator apparatus comprising:
   at least one sensor; and
   a controller coupled to the sensor and configured to:
      control servo-ventilation of the patient through the patient interface with a flow of pressurized air in accordance with a target ventilation;
      set an initial target ventilation, a final target ventilation and a target ventilation ramp time; and
      control changes to the target ventilation based on the initial target ventilation, the final target ventilation, and the target ventilation ramp time, the target ventilation being programmed to increase over the target ventilation ramp time until the target ventilation reaches the final target ventilation, whereupon the target ventilation stays constant thereafter,
   wherein the target ventilation is either (a) a target minute ventilation or (b) a target tidal volume,
   wherein the target ventilation ramp time is at least days long to prevent glottic closure or cessation of respiratory drive;
   wherein to control changes to the target ventilation the controller is configured to calculate a rate of increase by calculating either of: (1) a ratio of (a) a difference between an initial target minute ventilation and a final target minute ventilation, and (b) the target ventilation ramp time; and (2) a ratio of (a) a difference between an initial target tidal volume and a final target tidal volume, and (b) the target ventilation ramp time, and
   wherein the controller is configured to lower the rate of increase of the target ventilation if a pressure support level is above a predetermined threshold associated with glottic closure or cessation of respiratory drive in order to prevent glottic closure or cessation of respiratory drive.

2. The servo-ventilator apparatus of claim 1 wherein the target ventilation is programmed to stay constant at a level of the initial target ventilation for a predetermined initial hold time.

3. The servo-ventilator apparatus of claim 1 wherein the controller is further configured to:
   set the initial target ventilation to a proportion of the patient's awake ventilation;
   set the final target ventilation to the initial target ventilation multiplied by a ratio of a current partial pressure of carbon dioxide (PCO2) value to a desired PCO2 value; and
   set the target ventilation ramp time to a value depending on a clinical urgency of lowering the current PCO2 and an amount by which it is desired to lower the current PCO2.

4. The servo-ventilator apparatus of claim 1 wherein the target ventilation is programmed to increase over the target ventilation ramp time at a constant rate.

5. The servo-ventilator apparatus of claim 1 wherein the rate of increase of the target ventilation is lowered so that the servo-ventilator apparatus takes longer to reach the final target ventilation.

6. The servo-ventilator apparatus of claim 1 wherein the rate of increase of the target ventilation is changed to zero temporarily.

7. The servo-ventilator apparatus of claim 1 wherein the rate of increase is changed such that the final target ventilation is never reached.

8. The servo-ventilator apparatus of claim 1 further comprising a sensor for sensing at least one of ventilation data and oxygen saturation data,
   wherein the controller sets the initial target ventilation and the final target ventilation based on the sensed at least one of ventilation data and oxygen saturation data.

9. The servo-ventilator apparatus of claim 1 wherein the controller is further configured to control changes to the target ventilation based on an increasing function of time, and
   wherein the target ventilation is programmed to increase according to the increasing function of time.

10. The servo-ventilator apparatus of claim 1 wherein the controller is further configured to deliver a minimal degree of ventilation support to the patient and set the target ventilation for use during sleep based upon ventilation data and patient oxygen saturation data measured by an oximeter.

11. The servo-ventilator apparatus of claim 1 wherein the target ventilation is the target minute ventilation.

12. The servo-ventilator apparatus of claim 11 wherein the controller is configured to calculate the ratio of (a) the difference between the initial target minute ventilation and the final target minute ventilation, and (b) the target ventilation ramp time.

13. The servo-ventilator apparatus of claim 1 wherein the target ventilation is the target tidal volume.

14. The servo-ventilator apparatus of claim 13 wherein the controller is configured to calculate the ratio of (a) the difference between the initial target tidal volume and the final target tidal volume, and (b) the target ventilation ramp time.

15. A method of servo-ventilator control for an apparatus for providing pressure support ventilation to a patient with alveolar hypoventilation during sleep, the method comprising:
   controlling servo-ventilation of the patient with a servo-ventilator through a patient interface with a flow of pressurized air in accordance with a target ventilation; and
   setting an initial target ventilation, a final target ventilation and a target ventilation ramp time;
   with a controller of the servo-ventilator, controlling changes to the target ventilation based on the initial target ventilation, the final target ventilation and the target ventilation ramp time, the target ventilation increasing over the target ventilation ramp time until the target ventilation reaches the final target ventilation, whereupon the target ventilation stays constant thereafter; and
   lowering a rate of increase of the target ventilation if a pressure support level is above a predetermined threshold associated with glottic closure or cessation of respiratory drive in order to prevent glottic closure or cessation of respiratory drive,
   wherein the target ventilation is either (a) a target minute ventilation or (b) a target tidal volume,
   wherein the target ventilation ramp time is at least days long to prevent glottic closure or cessation of respiratory drive, and
   wherein to control the changes to the target ventilation the controller determines the rate of increase by calculating either of: (1) a ratio of (a) a difference between an initial target minute ventilation and a final target minute ventilation, and (b) the target ventilation ramp time; and (2) a ratio of (a) a difference between an initial target tidal volume and a final target tidal volume, and (b) the target ventilation ramp time.

16. The method of claim 15 wherein the target ventilation stays constant at a level of the initial target ventilation for a predetermined initial hold time.

17. The method of claim 15 further comprising:
   setting the initial target ventilation to a proportion of the patient's awake ventilation;
   setting the final target ventilation to the initial target ventilation multiplied by a ratio of a current partial pressure of carbon dioxide (PCO2) value to a desired PCO2 value; and
   setting the target ventilation ramp time to a value depending on a clinical urgency of lowering the current PCO2 and an amount by which it is desired to lower the current PCO2.

18. The method of claim 15 wherein the target ventilation increases over the target ventilation ramp time at a constant rate.

19. The method of claim 15 further comprising lowering the rate of increase of the target ventilation so that the servo-ventilator takes longer to reach the final target ventilation.

20. The method of claim 15 further comprising changing the rate of increase of the target ventilation to zero temporarily.

21. The method of claim 15 further comprising changing the rate of increase such that the final target ventilation is never reached.

22. The method of claim 15 further comprising sensing at least one of ventilation data and oxygen saturation data, and setting the initial target ventilation and the final target ventilation based on the sensing.

23. The method of claim 15 further comprising controlling changes to the target ventilation based on an increasing function of time,
   wherein the target ventilation increases according to the increasing function of time.

24. The method of claim 15 further comprising setting the target ventilation for use during sleep based upon ventilation data and measured oxygen saturation data.

25. The method of claim 15 wherein the target ventilation is the target minute ventilation.

26. The method of claim 25 wherein the controller calculates the ratio of (a) the difference between the initial target minute ventilation and the final target minute ventilation, and (b) the target ventilation ramp time.

27. The method of claim 15 wherein the target ventilation is the target tidal volume.

28. The method of claim 27 wherein the controller calculates the ratio of (a) the difference between the initial target tidal volume and the final target tidal volume, and (b) the target ventilation ramp time.

* * * * *